United States Patent [19]

Frisbie et al.

[11] Patent Number: 5,226,421
[45] Date of Patent: Jul. 13, 1993

[54] DOPPLER ELONGATE FLEXIBLE MEMBER HAVING AN INFLATABLE BALLOON MOUNTED THEREON

[75] Inventors: Jeffrey Frisbie, San Jose; Menahem F. Nassi, Palo Alto, both of Calif.

[73] Assignee: Cardiometrics, Inc., Mountain View, Calif.

[21] Appl. No.: 848,428

[22] Filed: Mar. 6, 1992

[51] Int. Cl.⁵ .................................. A61B 8/12
[52] U.S. Cl. .................... 128/662.04; 128/662.06; 128/772; 128/692; 128/661.09
[58] Field of Search .............. 128/661.07, 661.08, 128/661.09, 662.06, 692, 772, 662.04

[56] References Cited

U.S. PATENT DOCUMENTS

| | | | |
|---|---|---|---|
| 4,582,181 | 4/1986 | Samson | 128/348.1 |
| 4,967,753 | 11/1990 | Haase et al. | 128/772 |
| 4,991,588 | 2/1991 | Pflueger et al. | 128/772 |
| 5,046,503 | 9/1991 | Schneiderman | 128/662.06 |
| 5,059,851 | 11/1991 | Corl et al. | 310/334 |
| 5,100,424 | 3/1992 | Jang et al. | 128/662.06 |

Primary Examiner—Kyle L. Howell
Assistant Examiner—George Manuel
Attorney, Agent, or Firm—Flehr, Hohbach, Test, Albritton & Herbert

[57] ABSTRACT

A doppler guide wire having an inflatable balloon thereon which is inflatable with a balloon inflation medium. An elongate flexible member having proximal and distal extremities. An ultrasonic transducer is secured to the distal extremity of the elongate flexible member. An inflatable balloon mounted on the distal extremity of the elongate flexible member proximal of the ultrasonic transducer. A balloon inflation lumen opens into the interior of the balloon and extends along the length of the elongate flexible member. Conductors are connected to the ultrasonic transducer and extend along the length of the elongate flexible member.

6 Claims, 1 Drawing Sheet

DOPPLER ELONGATE FLEXIBLE MEMBER HAVING AN INFLATABLE BALLOON MOUNTED THEREON

This invention relates to a doppler guide wire having an inflatable balloon mounted thereon. Dilatation catheters have heretofore been provided as, for example, in U.S. Pat. No. 4,582,181. Doppler guide wires have been provided as, for example, in U.S. Pat. No. 5,059,851. However, a need has arisen for balloon dilatation catheters which have ultrasonic capabilities which requirements are not met by the devices disclosed in either of the cited patents. There is, therefore, a need for a doppler guide wire which has an inflatable balloon mounted thereon which meets these requirements.

In general, it is an object of the present invention to provide a doppler guide wire having an inflatable balloon mounted thereon.

Another object of the invention is to provide a guide wire of the above characters which has a small diameter so that it can be inserted into small and tortuous vessels.

Another object of the invention is to provide a guide wire of the above character which is very flexible.

Another object of the invention is to provide a guide wire of the above character in which the balloon can be readily inflated and deflated.

Another object of the invention is to provide a guide wire of the above character which facilitates the making of ultrasonic measurements to ascertain blood flow velocity.

Additional objects and features of the invention will appear from the following description in which the preferred embodiments are set forth in detail in conjunction with the accompanying drawings.

DETAILED DESCRIPTION OF THE INVENTION

In general, the doppler guide wire having an inflatable balloon mounted thereon is comprised of an elongate flexible guide wire having proximal and distal extremities. An ultrasonic transducer is provided. Means is provided for securing the ultrasonic transducer to the distal extremity of the guide wire. An inflatable balloon is mounted on the distal extremity of the guide wire proximal of the ultrasonic transducer. A lumen opening into the interior of the balloon extends along the length of the guide wire. Conductive means is connected to the ultrasonic transducer and extends along the length of the guide wire.

Figure 1:
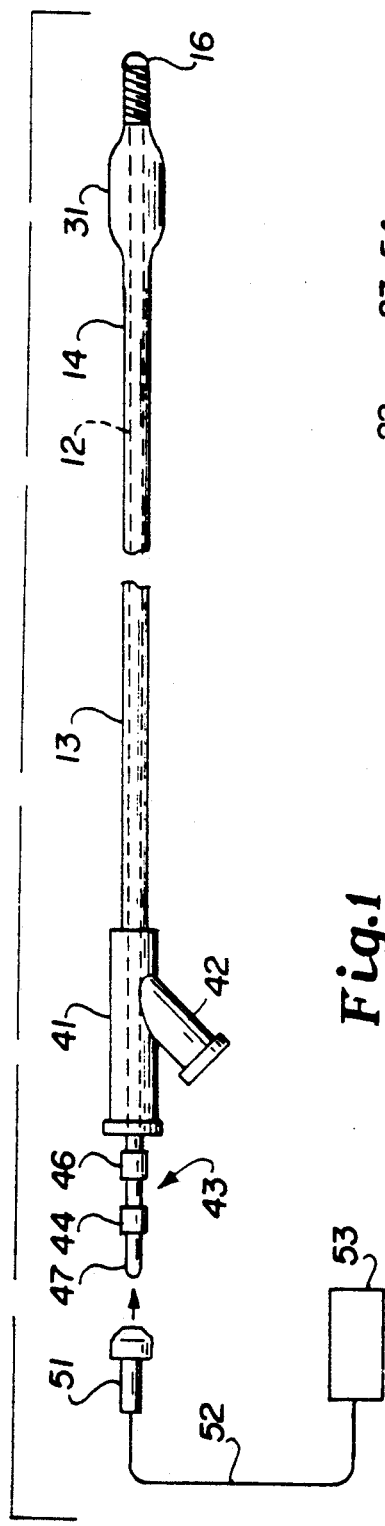
FIG. 1 is a side elevational view partially in cross-section of a doppler guide wire having an inflatable balloon mounted thereon and incorporating the present invention.
Figure 3:
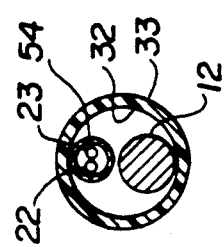
FIG. 3 is a cross sectional view taken along the line 3—3 of FIG. 2.
Figure 2:
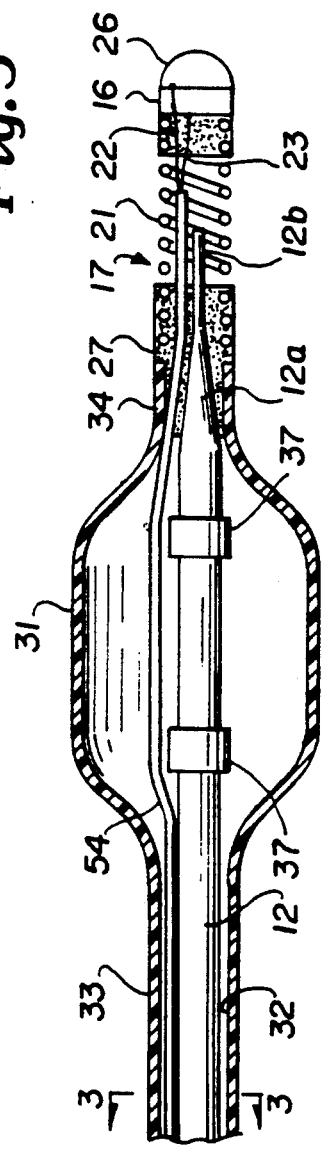
FIG. 2 is an enlarged detail view of the distal extremity of the guide wire shown in FIG. 1.

More specifically, as shown in FIGS. 1 and 2 of the drawings, the doppler guide wire 11 having an inflatable balloon mounted thereon consists of a elongate flexible member 12 serving as a guide wire having proximal and distal extremities 13 and 14. It can have a suitable length as, for example, 150 centimeters and a suitable diameter ranging from 0.025" to 0.010". The elongate flexible member 12 can be formed of a suitable material such as solid stainless steel or, alternatively, as hereinafter described can be formed of a hollow stainless steel hypo-tube ranging in diameter from 0.025" to 0.010" with a wall thickness ranging from 0.001" to 0.003".

An ultrasonic transducer 16 of a suitable type such as disclosed in U.S. Pat. No. 5,059,851 is provided. Tip means 17 is provided for flexibly securing the ultrasonic transducer 16 to the distal extremity 14 of the elongate flexible member 12. In order to impart additional flexibility to the tip means 17, the distal extremity 14 of the elongate flexible member 12 is provided with a tapered portion 12a as, for example, of a length 2 to 10 centimeters in which the diameter is tapered down from the original diameter of the elongate flexible member 12 to a diameter of 0.002" to 0.008" which leads into a flattened portion 12b having a thickness ranging 0.001"×0.004" and having a length of 1 to 4 centimeters. A coil spring 21 is provided having a suitable length as, for example, 2 to 10 centimeters and is formed of a material which is preferably radiopaque such as tungsten, platinum, palladium or alloys thereof. The transducer can have a diameter ranging from 0.030" to 0.010".

First and second conductors 22 and 23 forming conductor means are connected to the front and back sides of the ultrasonic transducer 16 and extend proximally from the transducer 16 through the coil 21. The transducer 16 is secured to the distal extremity of the coil 21 by suitable means such as an adhesive 24 through which the conductors 22 and 23 extend as shown in FIG. 2. A hemispherical lens 26 is provided on the front surface of the ultrasonic transducer 16 and is formed of a suitable material such as an epoxy.

The proximal extremity of the coil spring 21 is secured to the tapered portion 12a of the distal extremity 14 of the elongate flexible member 12 by suitable means such as an adhesive 27 so that at least a portion of the elongate flexible member 12 is free of adhesive, as shown in FIG. 2.

It should be appreciated that the means shown for attaching the transducer 16 to the coil or coil spring 21 is only one of several different types of constructions which can be utilized. For example, as disclosed in U.S. Pat. No. 5,059,851, the transducer 16 can be provided in a cylinder (not shown) which is secured to the spring. Alternatively, the transducer 16 can be encapsulated within the distal extremity of the spring 21 or encapsulated so that it is positioned forward or distal of the spring 21

An inflatable balloon 31 is mounted on the distal extremity 14 of the elongate flexible member 12. The balloon 31 can be fabricated from a suitable material such as a heat shrinkable polyethylene which can have a suitable inflated diameter as, for example, ranging from 3.0 to 1.5 millimeters. The balloon 31 when inflated is generally cylindrical as shown. A balloon inflation lumen 32 is provided which opens into the interior of the balloon 31 and extends along the length of the elongate flexible member 12. As shown in FIG. 2, the balloon inflation lumen 32 is provided by a flexible elongate tubular member 33 which extends coaxially of the elongate flexible member 12 so that the annular balloon inflation lumen 32 extends substantially the entire length of the elongate flexible member 12. The balloon 31 can be formed integral with the distal extremity of the tubular member 33. The distal extremity 34 of the tubular member 33 distal of the balloon 31 is of reduced diameter and is secured to the distal extremity 14 of the elongate flexible member 12 by suitable means such as the adhesive 27 immediately proximal of the proximal extremity of the spring 21. The tubular member 33 can have a suitable diameter as, for example, 0.020" to 0.040" and, preferably, 0.025" to 0.035" with a wall thickness arranged from 0.001" to 0.005" to provide a lumen 32 ranging from 0.015" to 0.033". An annular space within lumen 32 of at least 0.001 inches should be provided for inflating and deflating the balloon 31 with the inflation medium. Spaced apart bands 37 of a suitable radiopaque material such as gold can be provided within the interior of the balloon 31 adjacent the opposite ends of the same to aid in visualizing the position of the balloon 31 during a medical procedure.

Also, it should be appreciated that the distal portion 14 of the elongate flexible member 12 can be of a greater length so that it extends into the adhesive 24 provided for adhering the ultrasonic transducer 16 to the distal extremity of the coil spring 21.

A "y" adapter 41 is provided at the proximal extremity of the elongate flexible member 12 which has the inflation lumen 32 in communication with a port 42 provided on the adapter 41. A male electrical connector 43 is provided consisting of spaced apart electrical contacts 44 and 46 mounted on a tubular insulating number 47 carried by the proximal extremity of the elongate flexible member 12 and connected to the conductors 22 and 23 so that an electrical connection can be made to the ultrasonic transducer 16 for making ultrasonic measurements. The adapter 41 forms a fluid-tight seal with the tubular number 47. The male connector 43 is adapted to be used with a combination connector and torque device 51 of the type described in corresponding application Ser. No. 549,227 filed Jul. 6, 1990. The device 51 is connected by a cable 52 to a connector 53. The connector 53 is adapted to be connected to suitable instrumentation (not shown).

The conductors 22 and 23 extend therethrough the inflation lumen 32 and insulated from each other, the inflation medium, and from the elongate flexible member 12. The conductors can be left loose in the annular lumen or, alternatively, they can be affixed at spaced apart points longitudinally of the elongate flexible member 12. Also, if desired, the conductors 22 and 23 can be secured to the wall of the tubular member 33. In order to provide further protection from the inflation medium, the conductors 22 and 23 can be shielded by an additional flexible, tubular sheath 51 formed of a suitable material such as plastic extending the length of the conductors 22 and 23.

Operation and use of the doppler guide wire 11 may now be briefly described as follows. Let it be assumed that it is desired to perform an angioplasty procedure. The guide wire is advanced through a guiding catheter with the balloon 31 in a collapsed or deflated position until the balloon traverses across the lesion or stenosis to be dilated. The torque device 51 can be used to rotate the distal extremity 14 of the elongate flexible member and the transducer 16 to aid in advancing the guide wire through a tortuous vessel. The positioning of the balloon 31 can be ascertained by observing the position of the radiopaque coil spring 21 and in addition, or alternatively, by visualizing the radiopaque bands 37 in the balloon to properly position the balloon with respect to the stenosis. It should be appreciated that blood velocity measurements can be made by use of the transducer 16 to indicate blood flow in the vicinity of the stenosis before the balloon 31 crosses the stenosis and after the balloon 31 has crossed the stenosis before inflation of the balloon. Thereafter, the balloon 31 can be inflated to compress the atherosclerotic material in an attempt to provide an increased opening in the stenosis. The balloon 3; can then be deflated and another blood flow velocity measurement made to ascertain whether or not increased flow has been provided.

If a still further increase in flow is desired in the vessel, the balloon 31 can be reinflated for an appropriate period of time to again compress the atherosclerotic material. Another velocity measurement can then be made. This procedure can be continued until the desired flow is obtained. Alternatively, the deflated balloon can be withdrawn from the region which inflation has occurred and another velocity measurement made to ascertain the change in velocity of blood flow prior to and after the balloon inflations have occurred to ascertain the efficacy of the procedure performed.

After it has been ascertained that the maximum performance has been achieved with the doppler guide wire, the doppler guide wire can be removed in a conventional manner.

During blood flow velocity measurements, it may be desirable to rotate the transducer 16 by use of the torque device 51 to optimize the received signal from the transducer 16.

It is apparent from the foregoing that there has been provided a doppler guide wire which can be used for angioplasty which makes it possible to make on-the-spot velocity measurements to ascertain the efficacy of the procedure being performed. The guide wires are of small diameter so that very small and tortuous vessels having stenoses therein can be treated. The guide wire has a very flexible tip making it possible to negotiate small and tortuous vessels, in particular, by the flexible coil spring 21 used for mounting the ultrasonic transducer and by the use of the torque device 51.

What is claimed is:

1. In a doppler guide wire having an inflatable balloon secured thereon which is inflatable with a balloon inflation medium, an elongate flexible member having proximal and distal extremities, an ultrasonic transducer, means securing the ultrasonic transducer to the distal extremity of the elongate flexible member, said inflatable balloon fixedly mounted on the distal extremity of the elongate flexible member proximal of the ultrasonic transducer, a balloon inflation lumen opening into the interior of the balloon and extending along the length of the elongate flexible member for introducing the balloon inflation medium into the balloon and conductor means connected to the ultrasonic transducer and extending along the length of the elongate flexible member.

2. A guide wire as in claim 1, wherein said balloon inflation lumen is formed by a tubular member extending coaxially over the elongate flexible element to provide an annular lumen extending into the interior of the balloon.

3. A guide wire as in claim 2, wherein said conductor means extends through the balloon inflation lumen.

4. A guide wire as in claim 3 together with a protective sheath enclosing the conductor means for protecting the conductor means from the balloon inflation medium.

5. A guide wire as in claim 1, wherein said tubular member and said balloon are formed integral with each other.

6. A guide wire as in claim 1, wherein said means for securing ultrasonic transducer to the distal extremity of the elongate flexible element includes a coil spring.

* * * * *

UNITED STATES PATENT AND TRADEMARK OFFICE
CERTIFICATE OF CORRECTION

PATENT NO. : 5,226,421
DATED : July 13, 1993
INVENTOR(S) : Jeffrey Frisbie, et al.

It is certified that error appears in the above-identified patent and that said Letters Patent is hereby corrected as shown below:

Column 3, line 24: change "number" to --member--.

Column 3, line 29: change "number" to --member--.

Column 3, line 46: change "sheath 51" to --sheath 54--.

Column 4, lines 2-3: change "balloon 3; can" to --balloon 31 can--.

Signed and Sealed this

Sixteenth Day of August, 1994

Attest:

BRUCE LEHMAN

Attesting Officer       Commissioner of Patents and Trademarks